United States Patent [19]

Sawin et al.

[11] Patent Number: 5,733,534
[45] Date of Patent: *Mar. 31, 1998

[54] ANTIPERSPIRANT STICK COMPOSITIONS EXHIBITING IMPROVED WASH-OFF PERFORMANCE

[75] Inventors: Philip Andrew Sawin, Cincinnati, Ohio; John Paul Luebbe, Lawrenceburg, Ind.

[73] Assignee: The Procter & Gamble Company, Cincinnati, Ohio

[*] Notice: The term of this patent shall not extend beyond the expiration date of Pat. No. 5,429,816.

[21] Appl. No.: 390,901

[22] Filed: Feb. 16, 1995

Related U.S. Application Data

[63] Continuation of Ser. No. 110,596, Aug. 23, 1993, abandoned, which is a continuation-in-part of Ser. No. 53,618, Apr. 27, 1993, abandoned.

[51] Int. Cl.$^6$ .................................................. A61K 7/32
[52] U.S. Cl. ........................... 424/65; 424/66; 424/68; 424/DIG. 5; 514/944
[58] Field of Search ........................... 424/65, 66, 68, 424/69, 401, DIG. 5; 514/944

[56] References Cited

U.S. PATENT DOCUMENTS

| | | | |
|---|---|---|---|
| 2,900,306 | 8/1959 | Slater | 424/65 |
| 3,255,082 | 6/1966 | Barton | 424/68 |
| 3,903,258 | 9/1975 | Siegal | 424/66 |
| 3,904,741 | 9/1975 | Jones et al. | 423/462 |
| 3,969,087 | 7/1976 | Saito et al. | 44/270 |
| 3,970,748 | 7/1976 | Mecca | 424/68 |
| 3,979,510 | 9/1976 | Rubino | 424/47 |
| 3,981,896 | 9/1976 | Pauling | 556/10 |
| 4,017,599 | 4/1977 | Rubino | 424/47 |
| 4,049,792 | 9/1977 | Elsnau | 424/68 |
| 4,126,679 | 11/1987 | Davy et al. | 424/66 |
| 4,137,306 | 1/1979 | Rubino et al. | 424/68 |
| 4,151,272 | 4/1979 | Geary et al. | 424/68 |
| 4,154,816 | 5/1979 | Roehl et al. | 424/68 |
| 4,202,879 | 5/1980 | Shelton | 424/66 |
| 4,226,889 | 10/1980 | Yuhas | 424/59 |
| 4,371,645 | 2/1983 | Mahaffey, Jr. | 524/108 |
| 4,518,582 | 5/1985 | Schamper et al. | 424/66 |
| 4,719,102 | 1/1988 | Randhawa et al. | 424/66 |
| 4,722,835 | 2/1988 | Schamper et al. | 424/66 |
| 4,722,836 | 2/1988 | Geary et al. | 424/68 |
| 4,724,139 | 2/1988 | Palinczar | 424/66 |
| 4,725,430 | 2/1988 | Schamper et al. | 424/66 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,822,603 | 4/1989 | Farris et al. | 424/66 |
| 4,919,934 | 4/1990 | Deckner et al. | 424/401 |
| 4,944,937 | 7/1990 | McCall | 424/65 |
| 4,948,578 | 8/1990 | Burger et al. | 424/68 |
| 4,985,238 | 1/1991 | Tanner et al. | 424/66 |
| 5,019,375 | 5/1991 | Tanner et al. | 424/66 |
| 5,429,816 | 7/1995 | Hofrichter et al. | 424/66 |

FOREIGN PATENT DOCUMENTS

| | | |
|---|---|---|
| 1164347 | 3/1984 | Canada . |
| 117070 | 8/1984 | European Pat. Off. . |
| 0 295 071 | 12/1988 | European Pat. Off. . |
| 0373 499 | 6/1990 | European Pat. Off. . |
| 0396 137 | 11/1990 | European Pat. Off. . |
| 0 448 278 | 9/1991 | European Pat. Off. . |
| 64-62377 | 3/1989 | Japan . |
| 1-207223 | 8/1989 | Japan . |
| 2-180805 | 7/1990 | Japan . |
| 2-264707 | 10/1990 | Japan . |

OTHER PUBLICATIONS

C. D. Vaughn, "Solubility Effects in Product, Package, Penetration and Preservation" 103 *Cosmetics and Toiletries* 47–69, Oct. 1988.

Todd et al., "Volatile Silicone Fluids for Cosmetics", 91 *Cosmetics and Toiletries*, 27–32, Jan. (1976).

S/N 370,559, 6/23/89, Smith & Ward.

*Primary Examiner*—John C. Bleutge
*Assistant Examiner*—Robert H. Harrison
*Attorney, Agent, or Firm*—William J. Winter; Anthony D. Sabatelli; Leonard W. Lewis

[57] ABSTRACT

Antiperspirant stick compositions made from a solidifying agent which may include a gellant such as n-acyl amino acid amides, 12-hydroxystearic acid, esters of 12-hydroxystearic acid, amides of 12-hydroxystearic acid, and mixtures thereof; or a wax; a liquid base material including a non-volatile, non-polar emollient oil; an antiperspirant active; and a wash-off agent made of selected polyoxyethylene ethers; polyoxyethylene esters and diesters; and polyoxyethylene glyceryl esters and diesters. Such antiperspirant stick compositions exhibit improved wash-off performance, particularly with regard to the solidifying agent and the non-polar, non-volatile oils. These compositions are easily prepared by conventional techniques.

19 Claims, No Drawings

1

ANTIPERSPIRANT STICK COMPOSITIONS EXHIBITING IMPROVED WASH-OFF PERFORMANCE

This is a continuation of application Ser. No. 08/110,596, filed on Aug. 23, 1993, abandoned which is a continuation-in-part of application Ser. No. 08/053,618, filed Apr. 27, 1993, now abandoned.

FIELD OF THE INVENTION

The present invention relates to antiperspirant compositions; and more particularly, to antiperspirant stick compositions.

BACKGROUND OF THE INVENTION

Personal hygienic habits typically include a means for reducing human body odors. These habits include routine bathing or washing the body; particularly the axilla. Typically, the axilla is also treated with compositions to retard odor formation, such as antiperspirant compositions. Generally, various ingredients from the antiperspirant composition remain on the skin from the previous application at the time washing of the axilla occurs. Thus, it is highly desirable that the ingredients within the antiperspirant composition—particularly those which might impart a sticky, or tacky feel to the axilla—are readily washed off.

Antiperspirant compositions are well known in the art, and generally include an astringent material in a suitable carrier. Astringent materials typically used in antiperspirants are metal salts, particularly aluminum and zinc metal complexes. Said metal salts is disclosed in Plechner, *Antiperspirants and Deodorants*, 2 Cosmetics, Science and Technology, Balsam and Sagarin, 374–400, 1972; incorporated herein by reference.

Antiperspirant compositions can take a number of different forms, each dependent on the ingredients used in addition to the above mentioned astringent metallic salts. The forms include lotions, solid sticks, and creams; the most popular being solid sticks. Solid stick antiperspirant compositions include wax sticks and gel sticks.

Antiperspirant gel sticks utilize a gellant as a solidifying agent to impart the solid stick structure to the composition. Similarly, antiperspirant wax sticks utilize an aliphatic alcohol wax as a solidifying agent. In addition, antiperspirant sticks generally include non-volatile emollients to provide desirable aesthetic characteristics (e.g., not having a sticky, tacky and/or wet feel). Unfortunately, the combination of solidifying agents with the non-volatile emollients can be resistant to being washed off the skin after use. The present invention, however, solves this problem by improving the wash-off performance of such sticks.

SUMMARY OF THE INVENTION

Antiperspirant stick compositions which exhibit improved wash-off performance are provided. In accordance with one aspect of the present invention the composition includes:

a. a solidifying agent;

b. a liquid base material including a non-polar, non-volatile emollient;

c. an antiperspirant active; and d. a wash-off agent selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene diesters having the formula $R_1CO(OCH_2CH_2)_nOH$; polyoxyethylene esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$ wherein:

$R_1$ is an alkyl, alkenyl, or aromatic hydrocarbon radical having from about 4 to about 50 carbon atoms; $R_2$ is an identical or different alkyl, alkenyl, or aromatic hydrocarbon radical having from about 4 to about 22 carbon atoms; n is from about 2 to about 80; and wherein the wash-off agent has a solubility parameter of at least about 7.

All percentages herein are by weight of the total composition and all ratios are weight ratios unless otherwise indicated. Unless otherwise indicated, all percentages, ratios, and levels of ingredients referred to herein are based upon the actual amount of the ingredient, and do not include solvents, fillers, or other materials with which the ingredient may be combined when supplied commercially.

All documents referred to herein, including all patents, all patent applications and all articles, are hereby incorporated herein by reference in their entirety.

DETAILED DESCRIPTION OF THE INVENTION

Antiperspirant stick compositions of the present invention which exhibit improved wash-off performance may comprise, consist of, or consist essentially of the essential elements described herein as well as one or more of the preferred or optional ingredients described herein.

A. Solidifying Agents

A variety of materials can function as solidifying agents in compositions of the present invention. The term "solidifying agent" as used herein means materials which are effective at physically and/or chemically altering the liquid base material so as to form a final stick composition which is a stable stick at ambient conditions and is deposited on the skin during normal use conditions. Although the term "stick" as utilized herein includes semi-solid forms (i.e., preferably having a viscosity of at least about 1,000,000 centipoise at 25° C.), solid forms (i.e., preferably having an average penetration value within a given production batch from about 3 to about 25 mm over a period of 5 seconds as measured utilizing American Society for Testing Materials (ASTM) Method D-5, with a penetration cone (Model H1312; sold by Humbolt Manufacturing Company) weighing 2.0 g (making the total mass 50 g) and a Sommer & Runge Model PNR10 Penetrometer) are preferred.

Solidifying agents are themselves solids at ambient conditions. The level of the solidifying agent in antiperspirant stick compositions of the present invention is preferably from about 1% to about 25%. When the solidifying agent is a wax as described below the level of solidifying agent is more preferably from about 10% to about 20%; and even more preferably, from about 10% to about 15%. When the solidifying agent is a gellant as described below the level of the solidifying agent is more preferably from about 3% to about 12%; and even more preferably from about 5% to about 10%.

1. Waxes as Solidifying Agents

Waxes are frequently used as solidifying agents in antiperspirant stick compositions which are commonly referred to as wax sticks. Particularly useful are waxes having a low melting point, i.e., having a melting point of from about 37° C. to 75° C. Such low melting point waxes are well known in the art and include fatty acids, fatty alcohols, fatty acid esters, fatty add amides; acid preferably having fatty chains from about 8 to about 30 carbon atoms, and more preferably from about 12 to about 22 carbon atoms. Preferred low melting point waxes include cetyl alcohol, palmitic acid, myristyl alcohol, stearyl alcohol, behenyl alcohol, paraffin, and mixtures thereof. Additional useful waxes are disclosed in U.S. Pat. No. 4,822,603 issued to Farris et al on Apr. 18, 1989; U.S. Pat. No. 4,919,934 issued to Deckner on Apr. 24, 1990; and U.S. Pat. No. 4,944,937 issued to McCall on Jul. 31, 1990.

In addition, secondary waxes having a high melting point, i.e., having a melting point of from above 75° C. to about 130° C., may optionally be utilized. These high melting point waxes are preferably present at levels up to about 7%. Such waxes include beeswax, carnauba, baysberry, canelilla, montan, ozokerite, ceresin, hydrogenated castor oil (castor wax), synthetic waxes such as Fisher-Tropsch waxes, microcrystalline waxes, and mixtures thereof. Additional useful high melting point waxes are disclosed in U.S. Pat. No. 4,049,792 which issued to Elsnau on Sep. 20, 1977.

2. Gellants as Solidifying Agents

Gel sticks utilize gellants as solidifying agents. Typical Gellants include fatty acid soaps and dibenzylidine alditol acetals. The following patents are illustrative of various fatty acid soap gellants: U.S. Pat. No. 2,900,306 issued to Slater on Aug. 18. 1959; U.S. Pat. No. 3,255,082 issued to Barton on Jun. 7, 1966; U.S. Pat. No. 4,137,306 issued to Rubino on Jan. 30, 1979; U.S. Pat. No. 4,226,889 issued to Yuhas on Oct. 7, 1980; U.S. Pat. No. 4,944,937 issued to McCall on Jul. 31, 1990. The following patents are illustrative of dibenzylidine monosorbitol acetal gellants: U.S. Pat. No. 4,154,816 issued to Roehl et al. on May 15, 1979; U.S. Pat. No. 4,371,645 issued to Mahaffey on Feb. 1, 1983; U.S. Pat. No. 4,518,582 issued to Schamper et al on May 21, 1985; U.S. Pat. No. 4,719,102 issued to Randhawa et al. on Jan. 12, 1988; U.S. Pat. No. 4,722,835 issued to Schamper et al on Feb. 2, 1988; U.S. Pat. No. 4,725,430 issued to Schamper et al on Feb. 16, 1988; U.S. Pat. No. 4,781,917 issued to Luebbe et al. on Nov. 1, 1988; U.S. Pat. No. 4,816,261 issued to Luebbe et al. on Mar. 28, 1989; U.S. Pat. No. 4,822,602 issued to Sabetelli on Apr. 18, 1989; and Japanese Application 64–62377 published Mar. 8, 1989. Additional gellants are disclosed in such references as European Patent Application (EPO) 0 448 278 which published Sep. 29, 1991; EPO 0 373 499 which published Jun. 20, 1988; EPO 0 396 137 which published Nov. 7 1990; and U.S. Pat. No. 4,948,578 which issued to Burger et al. on Aug. 14, 1990.

Highly preferred gellants are selected from the group consisting of n-acyl amino acid amides, 12-hydroxystearic acid, esters of 12-hydroxystearic acid, amides of 12-hydroxystearic acid, and mixtures thereof. When a mixture of a n-acyl amino acid amide with 12-hydroxystearic acid, esters of 12-hydroxystearic acid, or amides of 12-hydroxystearic acid is the gellant, the ratio of n-acyl amino acid amide to the 12-hydroxystearic acid, esters of 12-hydroxystearic acid, and/or amides of 12-hydroxystearic acid is preferably from about 1:20 to about 2:1; more preferably from about 1:10 to about 1:1; and most preferably from about 1:7 to about 1:2; and the level of n-acyl amino acid amide is at least about 0.1% total weight of the gel stick composition.

The preferred n-acyl amino acid amides are prepared from glutamic acid, lysine, glutamine, aspartic acid and mixtures thereof. Particularly preferred are n-acyl glutamic acid amides corresponding to the following formula:

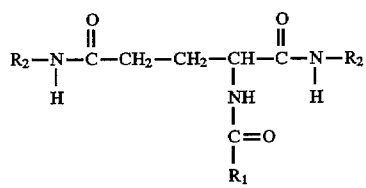

wherein $R_1$ is an aliphatic hydrocarbon radical having from about 12 to about 22 carbon atoms, and $R_2$ is an aliphatic hydrocarbon radical having from about 2 to about 22 carbon atoms. Non-limiting examples of these include n-lauroyl-L-glutamic acid dibutyl aide, n-stearoyl-L-glutamic acid diheptyl amide, and mixtures thereof. Preferred are N-lauroyl-L-glutamic acid diethyl amide, N-lauroyl-L-glutamic acid dibutyl amide, N-lauroyl-L-glutamic acid diheptyl amide, N-lauroyl-L-glutamic acid dioctyl amide, N-lauroyl-L-glutamic acid didecyl amide, N-lauroyl-L-glutamic acid didecyl amide, N-lauroyl-L-glutamic acid ditetradecyl amide, N-lauroyl-L-glutamic acid dihexadecyl amide, N-lauroyl-L-glutamic acid distearyl amide, N-stearoyl-L-glutamic acid diethyl amide, N-stearoyl-L-glutamic acid dibutyl amide, N-stearoyl-L-glutamic acid diheptyl amide, N-stearoyl-L-glutamic acid dioctyl amide, N-stearoyl-L-glutamic acid didecyl amide, N-stearoyl-L-glutamic acid didecyl amide, N-stearoyl-L-glutamic acid ditetradecyl amide, N-stearoyl-L-glutamic acid dihexadecyl amide, N-stearoyl-L-glutamic acid distearyl amide. Most preferred is n-lauroyl-L-glutamic acid dibutyl amide. Additional information regarding the use of n-acyl amino acids as gellants are found in the following references: U.S. Pat. No. 3,969,087 issued on Jul. 13, 1976 to Saito et al.; Japanese Patent Application 1-207223 which published Aug. 21, 1989; and Japanese Patent Application 2-180805 which published Jul. 13, 1988.

Although sticks can be made solely with n-acyl amino acid amide, 12-hydroxystearic acid, esters of 12-hydroxystearic acid, amides of 12-hydroxystearic acid as the gellant, it has been found that incorporating 12-hydroxystearic acid, esters of 12-hydroxystearic acid, and/or amides of 12-hydroxystearic acid along with n-acyl amino acid amides into the gellant is advantageous. Preferred 12-hydroxystearic acid, esters of 12-hydroxystearic acid and amides of 12-hydroxystearic acid are isopropyl amide of 12-hydroxystearic acid, benzyl amide of 12-hydroxystearic acid, benzyl ester of 12-hydroxystearic acid, methyl ester of 12-hydroxystearic acid, ethyl ester of 12-hydroxystearic acid, isopropyl ester of 12-hydroxystearic acid, stearyl ester of 12-hydroxystearic acid.

When 12-hydroxystearic acid, esters of 12-hydroxystearic acid, and/or amides of 12-hydroxystearic acid is used in combination with the n-acyl amino acid amide, the level of gellant can be reduced while maintaining desirable stick characteristics such as hardness, low residue, and easy application qualities. Furthermore, the processing temperatures used to make the stick can be reduced. Lower processing temperatures reduce any tendency of the antiperspirant active and the perfumes to degrade during processing. Also, lower processing temperatures improve the compatibility of the above components with other stick components having lower boiling points, and packaging materials used to contain the stick.

B. Liquid Base Material

1. General

The base matrix of antiperspirant stick compositions of the present invention is formed by combining the above solidifying agent with a liquid base material. As used herein, the term "liquid" refers to materials which are liquids at ambient conditions and the term "liquid base material" includes all liquids within the composition except the wash-off agent described below. It is important that the liquid base material selected is of a type, and at such a level to sufficiently solubilize the solidifying agent when heated, and form a stick when cooled to ambient temperature. The liquid base material must be compatible with the solidifying agent so that the mixture of the two does not phase separate during processing. Furthermore, the liquid base materials are typically selected in order to provide aesthetic benefits, such as emolliency, low tack or minimized visible residue, without substantial interference with the effectiveness of the antiperspirant active component. Lastly, the particular liquid base material should be safe for application to human skin.

The liquid base materials include one or more non-polar emollients which have a solubility parameter from about 5 to about 11 (whether a wax or a gellant is used as the solidifying agent). When the solidifying agent is a gellant it is preferable that, in aggregate, the average solubility parameter of the liquid base material be from about 6 to about 10. Hence, a single non-polar emollient comprising the liquid base material may be used which itself has a solubility parameter in the range of from about 6 to about 10. Alternatively, a mixture of non-polar emollients may be used as the liquid base material herein, each having a solubility parameter in the range of from about 5 to about 11, such that the average solubility parameter of the mixture is from about 6 to about 10. Solubility parameters are common to the art of antiperspirant stick formulation and the means to determine them are disclosed by C. D. Vaughan, "Solubility Effects in Product, Package, Penetration and Preservation" 103 Cosmetics and Toiletries 47–69, October, 1988; and C. D. Vaughan, "Using Solubility Parameters in Cosmetics Formulation", 36 J Soc. Cosmetic Chemists 319–333, September/October, 1985.

The liquid base materials of the present invention are preferably used at levels from about 10% to about 95%; and more preferably from about 30% to about 80%. Included in the liquid base materials are one or more non-polar, non-volatile liquid emollients as described below preferably at levels from about 5% to about 60%; more preferably from about 5% to about 25%; and most preferably from about 7% to about 20%. Furthermore, the liquid base materials may optionally include one or more non-polar, volatile liquid emollients as described below. The volatile liquid emollients, when used, are preferably used at levels from about 10% to about 70%; more preferably, from about 25% to about 60%; and more preferably, from about 40% to about 60%.

2. Non-polar, Non-volatile Liquid Emollients

Non-polar, non-volatile liquid emollients useful in the present invention are disclosed in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et at. on Mar. 28, 1989. The term "non-volatile" as used herein refers to materials which exhibit a vapor pressure of no more than about 0.2 mm Hg at 25° C. at one atmosphere and/or to materials which have a boiling point at one atmosphere of at least about 300° C.

Non-polar, non-volatile liquid emollients useful in the present invention are preferably selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The emollients useful in the present invention may be either is saturated or unsaturated, have an aliphatic character and be straight or branched chained or contain alicyclic or aromatic rings. Preferably, the non-polar, non-volatile liquid emollients are selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof. More preferred are propoxylated ethers of $C_{14}$–$C_{18}$ fatty alcohols having a degree of propoxylation below about 50, esters of $C_2$–$C_8$ alcohols and $C_{12}$–$C_{26}$ carboxylic acids (e.g. ethyl myristate, isopropyl palmitate), esters of $C_{12}$–$C_{26}$ alcohols and benzoic acid (e.g. Finsolv TN supplied by Finetex), diesters of $C_2$–$C_8$ alcohols and adipic, sebacic, and phthalic acids (e.g., diisopropyl sebacate, diisopropyl adipate, di-n-butyl phthalate), polyhydric alcohol esters of $C_6$–$C_{26}$ carboxylic acids (e.g., propylene glycol dicaprate/ dicaprylate, propylene glycol isostearate); and mixtures thereof. Even more preferred are branched-chain aliphatic fatty alcohols having from about 12–26 carbon atoms. Even more preferred is hexyldecanol, octyldecanol, octyldodecanol and undecylpentadecanol; and most prefered is octyldodecanol. Such preferred aliphatic fatty alcohols are particularly useful in combination with the volatile liquid silicone oils discussed below to adjust the average solubility of the liquid base material.

The non-volatile silicone oils useful in the present invention are essentially non-volatile polyalkylsiloxanes selected from the group consisting of polyalkylsiloxanes, polyarylsiloxanes, polyalkylarylsiloxanes, polyethersiloxane copolymers, and mixtures thereof. Examples of these include polydimethyl siloxanes having viscosities of from about 5 to about 100,000 centistokes at 25° C. Among the preferred non-volatile silicone emollients useful in the present compositions are the polydimethyl siloxanes having viscosities from about 2 to about 400 centistokes at 25° C. Such polyalkylsiloxanes include the Viscasil series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991. Preferred mineral oils have the following properties:

(1) viscosity from about 5 centistokes to about 70 centistokes at 40° C.;

(2) density between about 0.82 and 0.89 g/cm3 at 25° C.;
(3) flash point between about 138° C. and about 216° C.; and
(4) carbon chain length between about 14 and about 40 carbon atoms.

Preferred branched chain hydrocarbon oils have the following properties:
(1) density between about 0.79 and about 0.89 g/cm3 at 20° C.
(2) boiling point greater than about 250° C.; and
(3) flash point between about 110° C. and about 200° C.

Particularly preferred branched-chain hydrocarbons include Permethyl 103A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

3. Non-polar, Volatile Liquid Emollients

The optional non-polar, volatile liquid emollients useful in the present invention are known in the art as disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. The term "volatile" as used herein refers to all materials which are not "non-volatile" as previously defined herein.

Non-polar, volatile liquid emollients particularly useful in the present invention are selected from the group consisting of silicone oils; hydrocarbons; and mixtures thereof. The emollients useful in the present invention may be either saturated or unsaturated, have an aliphatic character and be straight or branched chained or contain alicyclic or aromatic rings. Examples of volatile hydrocarbons include isodecane (such as Permethyl-99A which is available from Presperse Inc.) and the $C_7$–$C_8$ through $C_{12}$–$C_{15}$ isoparaffins (such as the Isopar Series available from Exxon Chemicals).

The volatile liquid silicone oils are particularly useful as the non-polar emollients in the liquid base material since they endow the antiperspirant stick composition with highly desirable aesthetics. Volatile silicone oils preferably comprise from about 10% to about 70%; more preferably, from about 25% to about 60%; more preferably from about 40% to about 60%; and most preferably, about 50%.

Volatile liquid silicone oils are disclosed in U.S. Pat. No. 4,781,917 issued to Luebbe et al. on Nov. 1, 1988. Additionally, a description of various volatile silicones materials is found in Todd et al., "Volatile Silicone Fluids for Cosmetics", Cosmetics and Toiletries, 91:27–32 (1976). Particularly preferred volatile silicone oils are selected from the group consisting of cyclic volatile silicones corresponding to the formula:

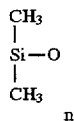

wherein n is from about 3 to about 7; and linear volatile silicones corresponding to the formula:

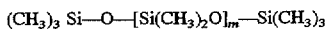

wherein m is from about 1 to about 7. Linear volatile silicones generally have viscosities of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

C. Antiperspirant Active

The compositions of the present invention also contain an astringent antiperspirant active. These actives are used at levels from about 0.5% to about 60%, preferably from about 5% to about 35%, of the antiperspirant gel stick composition. This active may be incorporated either in solubilized or particulate form. These weight percentages are calculated on an anhydrous metal salt basis (exclusive of glycine, the salts of glycine, or other complexing agents). If used in particulate form, the material preferably has a particle size of from about 1 to about 100 microns, preferably from about 1 to about 50 microns, and have a high bulk density (e.g., greater than about 0.7 g/cm3). Such materials include, for example, many aluminum or zirconium astringent salts or complexes and are well known in the antiperspirant art.

Any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

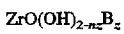

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various mounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068 issued to Luedders et al. on Feb. 12, 1974 discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by
(A) co-dissolving in water
  (1) one part $Al_2(OH)_{6-m}Q_m$, wherein Q is an anion selected from the group consisting of chloride, bromide and iodide, and m is a number from about 0.8 to about 2.0;
  (2) x parts $ZrO(OH)_{2-a}Q_a.nH_2O$, where Q is chloride, bromide or iodide; where a is from about 1 to about 2; where n is from about 1 to about 8; and where x has a value of from about 0.16 to about 1.2;
  (3) p parts neutral amino acid selected from the group consisting of glycine, dl-tryptophane, dl-b-phenylalanine, dl-valine, dl-methionine and b-alanine, and where p has a value of from about 0.06 to about 0.53;
(B) co-drying the resultant mixture to a friable solid; and
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599 issued to Rubino on Apr. 12, 1977.

A wide variety of other types of antiperspirant complexes are also known in the art. For example, U.S. Pat. No. 3,903,258 issued to Siegal on Sep. 2, 1975 discloses a zirconium aluminum complex prepared by reacting zirconyl chloride with aluminum hydroxide and aluminum chlorhydroxide. U.S. Pat. No. 3,979,510 issued to Rubino on Sep. 7, 1976 discloses an antiperspirant complex formed from certain aluminum compounds, certain zirconium compounds, and certain complex aluminum buffers. U.S. Pat. No. 3,981,896 issued to Pauling on Sep. 21, 1976 discloses an antiperspirant complex prepared from an aluminum polyol compound, a zirconium compound and an organic buffer. U.S. Pat. No. 3,970,748 issued to Mecca on Jul. 20, 1976 discloses an aluminum chlorhydroxy glycinate complex of the approximate general formula $[Al_2(OH)_4Cl][H_2CNH_2COOH]$.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

Solubilized antiperspirant actives which may be utilized in the present invention are also well known in the art. These materials utilize monohydric or polyhydric alcohols or water to solubilize the antiperspirant active before it is incorporated into the product. The levels of these polar solvents is less than 25%, and preferably less than 15% of the composition. Examples of such actives are taught, for example, in U.S. Pat. No. 4,137,306 issued to Rubino on Jan. 30, 1979; U.S. patent application Ser. No. 370,559, Smith and Ward, filed Jun. 23, 1989; and European Patent Application 0295070 which published Dec. 14, 1988.

D. Wash-off agent

The wash-off agent improves the ease with which the ingredients—particularly the solidifying agent and the nonpolar, non-volatile oils—may be washed off. The wash-off agent is highly preferably a non-liquid. In the case where the wash-off agent is a liquid, the wash-off agent should be miscible in the liquid base material and is not considered part of the liquid base material. The wash-off agent is preferably in the antiperspirant stick composition in an amount from about 0.1% to about 10%; preferably, from about 1% to about 5%; and more preferably, from about 1% to about 3%. The wash-off agent must be soluble in the amounts described above in the molten product matrix at reasonable process temperatures, i.e., preferably from about 80° C. to about 130° C.; more preferably from about 80° C. to about 110° C. Preferably the solubility parameter of the wash-off agent is at least about 7; more preferably, from about 7.5 to about 11. The wash-off agent of the present invention is—highly preferably, a non-liquid—selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene diesters having the formula $R_1CO(OCH_2CH_2)_nOOCR_2$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$—preferably, is the polyoxyethylene ethers—wherein:

$R_1$ is an alkyl, alkenyl, or aromatic hydrocarbon radical which may be substituted or unsubstituted—preferably an alkyl radical—having a lower limit of about 4 carbon atoms; preferably, about 12 carbon atoms; more preferably, about 14 carbon atoms; and most preferably, about 16 carbon atoms; and an upper limit of about 50 carbon atoms; more preferably, 35 carbon atoms; even more preferably, 22 carbon atoms; preferably, about 20 carbon atoms; and most preferably, about 18 carbon atoms; and wherein:

R2 is an identical or different alkyl, alkenyl, or aromatic hydrocarbon radical which may be substituted or unsubstituted—preferably an alkyl radical—having a lower limit of about 4 carbon atoms; preferably, about 12 carbon atoms; more preferably, about 14 carbon atoms; and most preferably, about 16 carbon atoms; and an upper limit of about 22 carbon atoms; preferably, about 20 carbon atoms; and most preferably, about 18 carbon atoms; and wherein:

n has a lower limit of about 2; preferably, about 4, more preferably, about 6; even more preferably, about 8; even more preferably, about 10 and most preferably, about 15; and wherein n has an upper limit of about 80; preferably, about 70; more preferably, about 60; even more preferably, about 50; even more preferably, about 40; even more preferably, about 30; and even more preferably, about 25.

Preferred examples of such wash-off agents include: ceteth-2 through ceteth-30, steareth-2 through steareth-30, ceteareth-2 through ceteareth-30, PEG-2 stearate through PEG-30 stearate, PEG-8 distearate, PEG-12 isostearate, C20–40 pareth-10, C20–40 pareth-40, PEG-16 hydrogenated castor oil, PEG-40 hydrogenated castor oil, and PEG-20 glyceryl stearate; more preferably, ceteareth-20, steareth-21, PEG-20 stearate, and PEG-16 hydrogenated castor oil; and most preferably, ceteareth-20.

E. Optional Ingredients

Antiperspirant stick compositions of the present invention may contain optional components which act as additional active or modify the physical characteristics of the composition or the components making up said compositions. Such components are well known in the art. A non-limiting group of these optional components include colorants, perfumes, thickeners, distributing agents, emulsifiers, bacteriostats, fungistats, and mixtures thereof. Optional components useful herein are described in the following references: U.S. Pat. No. 4,049,792 issued to Elsnau on Sep. 20, 1977; Canadian Patent 1,164,347 which issued to Beckmeyer et al. on Mar. 27, 1984; European Patent Application 117,070 which published on Aug. 29, 1984; and Geria, "Formulation of Stick Antiperspirants and Deodorants", *Cosmetics and Toiletries*, 99:55–60 (1984).

Thickeners are also useful in the present invention; particularly with gel sticks. Their selection and the level they are used at should be so as not to significantly affect the aesthetics of the stick composition. Typical levels of thickeners are at levels of less than about 5%. Examples of said thickeners are disclosed in U.S. Pat. No. 4,985,238 issued to Tanner et al. on Jan. 15, 1991. These thickeners include wax-like materials such as beeswax, cerasin, hydrogenated castor oil, synthetic waxes such as Fisher Tropsch waxes, microcrystalline waxes, polyethylene waxes, and mixtures thereof.

Particulate and filler materials may also be included in the present compositions. These materials are typically used at levels from about 0.5% to about 5%, preferably not more than 3%. Such materials are disclosed in U.S. Pat. No. 5,019,375, Tanner et al., issued May 28, 1991. Suitable filler materials include collodial silica (such as Cab-O-Sil, sold by Cabot Corp), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987. Examples of other particulate materials include particulate hydrophilic polymers such as cellulose ether polymers, modified starches, polyamides, and polypeptides.

METHODS OF MANUFACTURE

The present invention may be made by using any of the typical methods known to those skilled in the art, such as the methods disclosed in *Gels and Sticks Formulary*, 99 Cosmetics & Toiletries 77–84, 1984. Methods found particularly useful follow below:

Combine the solidifying agent, the liquid base material and the wash-off agent into a vessel equipped with a heat source. Heat the mixture to a temperature from about 80° C. to about 130° C. with stirring, until the mixture forms a clear homogeneous solution. Once clear, the solution is cooled and held at is approximately 65°–120° C. at which time the antiperspirant active (and other optional components such as filler powders or perfumes) is added into the above vessel and mixed thoroughly into the composition. The mixture is then poured into containers and allowed to cool. Upon cooling a stable antiperspirant stick is obtained. Alternatively, the antiperspirant active may be added along with the solidifying agent, the liquid base material and the wash-off agent in the first step.

METHODS FOR USE

The present invention provides methods for preventing perspiration and malodor associated with human perspiration. These methods comprise applying to the skin of a human a safe and effective amount of the antiperspirant as gel of the present invention. The term "a safe and effective amount" as used herein, is an amount which is effective in eliminating or substantially reducing malodor associated with human underarm perspiration while being safe for human use at a reasonable risk/benefit ratio. Typically, the safe and effective amount used is from about 0.1 gram per axilla to about 1.0 gram per axilla.

EXAMPLES

| | EXAMPLES | | | | | | | | |
|---|---|---|---|---|---|---|---|---|---|
| | I | II | III | IV | V | VI | VII | VIII | IX |
| N-lauroyl-L-glutamic acid-di-n-utylamide[1] | 2 | 1.33 | 2 | 2 | 2 | 2 | | 2 | 2 |
| 12-Hydroxystearic acid | 6 | 6.67 | 6 | 6 | 6 | 6 | | 6 | 6 |
| Stearyl alcohol | | | | | | | 13 | | |
| Cyclomethicone D-5[2] | 50 | 49 | 49 | 50 | 49 | 49 | 43 | 49 | 46.5 |
| Octyldodecanol[3] | 14 | 14 | 14 | | 14 | 14 | | 14 | 14 |
| Isocetyl alcohol | | | | 13 | | | | | |
| Polydecene[4] | | | | | | | 7 | | |
| Ceteareth-20 | 1.5 | 2.5 | 2.5 | 2.5 | | | 2.5 | | |
| Steareth-2 | | | | | 2.5 | | | | |
| Steareth-10 | | | | | | 2.5 | | | |
| PEG-8-Distearate | | | | | | | | | 5 |
| C20–40 Pareth-10[8] | | | | | | | | 1.25 | |
| C20–40 Pareth-40[9] | | | | | | | | 1.25 | |

-continued

|  | EXAMPLES | | | | | | | | |
| --- | --- | --- | --- | --- | --- | --- | --- | --- | --- |
|  | I | II | III | IV | V | VI | VII | VIII | IX |
| Alcohols C20–40[5] | 0.5 | 0.5 | 0.5 | 0.5 | 0.5 | 0.5 |  | 0.5 | 0.5 |
| Behenyl alcohol |  |  |  |  |  |  | 0.1 |  |  |
| Hydrogenated Castor Oil |  |  |  |  |  |  | 4 |  |  |
| Talc |  |  |  |  |  |  | 4 |  |  |
| Cab-O-sil[6] |  |  |  |  |  |  | 0.5 |  |  |
| Aluminum Zirconium Trichlorhydrex Gly[7] | 26 | 26 | 26 | 26 | 26 | 26 | 26 | 26 | 26 |

[1] GP-1 supplied by Ajinomoto Inc.
[2] Dow Corning 245 fluid - cyclic polydimethylsiloxane
[3] Eutanol-G supplied by Henkel Corp.
[4] Ehtylflo 364 supplied by Ethyl Corp.
[5] Unilin 425 supplied by Petrolite
[6] supplied by Cabot Corp.
[7] supplied by Westwood Chemical Co.
[8] Unithox 450 supplied by Petrolite
[9] Unithox 480 supplied by Petrolite The present examples are prepared utilizing the procedure outlined above in the section entitled "Methods of Manufacture".

The foregoing examples further describe and demonstrate embodiments within the scope of the present invention. These examples are solely for the purpose of illustration and are not to be construed as limitations of the present invention as many variations are possible without departing from the spirit or scope thereof. Accordingly, the present invention comprises all embodiments within the scope of the appended claims.

What is claimed is:

1. An antiperspirant stick composition comprising:
   a. from about 1% to about 25% of a gellant as a solidifying agent;
   b. from about 10% to about 95% of a liquid base material including a non-polar, non-volatile emollient having a solubility from about 5 to about 11;
   c. from about 0.5% to about 60% of an antiperspirant active; and
   d. from about 0.1% to about 10% of a wash-off agent selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene diesters having the formula $R_1CO(OCH_2CH_2)_nOOCR_2$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$ wherein:

$R_1$ is an alkyl, alkenyl, or aromatic hydrocarbon radical having from about 4 to about 50 carbon atoms; $R_2$ is an identical or different alkyl, alkenyl, or aromatic hydrocarbon radical having from about 4 to about 50 carbon atoms; n is from about 1 to about 80; and wherein the wash-off agent has a solubility parameter of at least about 7.

2. An antiperspirant stick composition according to claim 1 wherein the wash-off agent is selected from the group consisting of polyoxyethylene ethers having the formula $R_1(OCH_2CH_2)_nOH$; and wherein $R_1$ is an alkyl, alkenyl, or aromatic hydrocarbon radical having from about 12 to about 20 carbon atoms; and wherein n is from about 6 to about 50.

3. An antiperspirant stick composition according to claim 2 wherein $R_1$ is alkyl radical having from about 12 to about 20 carbon atoms; and wherein n is from about 6 to about 50.

4. An antiperspirant stick composition according to claim 1 wherein the wash-off agent is selected from the group consisting of steareth-2 through steareth-30, ceteareth-2 through ceteareth-30, PEG-2 stearate through PEG-30 stearate, PEG-8 distearate, PEG-12 isostearate, C20–40 pareth-10, C20–40 pareth-40, PEG-16 hydrogenated castor oil, PEG-40 hydrogenated castor oil, and PEG-20 glyceryl stearate, and mixtures thereof.

5. An antiperspirant stick composition according to claim 1 wherein the wash-off agent is present at levels from about 1% to about 5%.

6. An antiperspirant composition according to claim 5 wherein the wash-off agent is selected from the group consisting of polyoxyethylene ethers having the formula $R_1(OCH_2CH_2)_nOH$; and wherein $R_1$ is an alkyl, alkenyl, or aromatic hydrocarbon radical having from about 14 to about 20 carbon atoms; and wherein n is from about 6 to about 30.

7. An antiperspirant stick composition according to claim 5 wherein the gellant is selected from the group consisting of n-acyl amino acid amides, 12-hydroxystearic acid, esters of 12-hydroxystearic acid, amides of 12-hydroxystearic acid, and mixtures thereof.

8. An antiperspirant stick composition according to claim 6 wherein the gellant is selected from the group consisting of n-acyl amino acid amides, 12-hydroxystearic acid, esters of 12-hydroxystearic acid, amides of 12-hydroxystearic acid, and mixtures thereof.

9. An antiperspirant stick composition according to claim 7 wherein the liquid base material includes the non-polar, non-volatile emollient at a level from about 5% to about 60% of the antiperspirant stick composition; and wherein the liquid base material further includes a non-polar, volatile emollient at a level from about 10% to about 70% of the antiperspirant stick composition.

10. An antiperspirant stick composition according to claim 8 wherein the liquid base material includes the non-polar, non-volatile emollient at a level from about 5% to about 60% of the antiperspirant stick composition; and wherein the liquid base material further includes a non-polar, volatile emollient at a level from about 10% to about 70% of the antiperspirant stick composition.

11. An antiperspirant stick composition according to claim 9 wherein the non-polar, non-volatile emollient is selected from the group consisting of silicone oils; hydrocarbon oils; fatty alcohols; fatty acids; esters of mono and dibasic carboxylic acids with mono and polyhydric alcohols;

polyoxyethylenes; polyoxypropylenes; mixtures of polyoxyethylene and polyoxypropylene ethers of fatty alcohols; and mixtures thereof; and wherein the non-polar, volatile emollient is selected from the group consisting of silicone oils, hydrocarbons and mixtures thereof.

12. An antiperspirant stick composition according to claim 10 wherein the non-polar, non-volatile emolient is selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof; and wherein the non-polar, volatile emollient is selected from the group consisting of silicone oils, hydrocarbons and mixtures thereof.

13. An antiperspirant stick composition comprising:
   a. from about 3% to about 12% of a solidifying agent including an n-acyl amino acid amide gellant and an additional gellant selected from the group consisting of 12-hydroxystearic acid, esters of 12-hydroxystearic acid, amides of 12-hydroxystearic acid, and mixtures thereof; wherein the ratio of the n-acyl amino acid amide gellant to the 12-hydroxystearic acid, esters of 12-hydroxystearic acid, amides of 12-hydroxystearic acid, and mixtures thereof is from about 1:20 to about 2:1; and the level of n-acylamino acid amide is at least about 0.1% total weight of the stick;
   b. from about 30% to about 80% of a liquid base material including from about 5% to about 25% of the antiperspirant stick composition of a non-polar, non-volatile emollient; and including from about 25% to about 60% of a non-polar, volatile emollient;
   c. from about 5% to about 25% of an antiperspirant active; and
   d. from about 1% to about 5% of a wash-off agent selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene diesters having the formula $R_1CO(OCH_2CH_2)_nOOCR_2$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$ wherein:

$R_1$ is an alkyl, alkenyl, or aromatic hydrocarbon radical having from about 14 to about 22 carbon atoms; $R_2$ is an alkyl, alkenyl, or aromatic hydrocarbon radical having from about 14 to about 22 carbon atoms; and wherein n is from about 6 to about 50.

14. An antiperspirant composition according to claim 13 wherein the wash-off agent is selected from the group consisting of polyoxyethylene ethers having the formula $R_1(OCH_2CH_2)_nOH$; and wherein $R_1$ is an alkyl, alkenyl, or aromatic hydrocarbon radical having from about 14 to about 20 carbon atoms; and wherein n is from about 6 to about 30.

15. An antiperspirant composition according to claim 13 wherein the non-polar, non-volatile emollient is selected from the group consisting of aliphatic fatty alcohols having from about 12 to about 26 carbon atoms.

16. An antiperspirant composition according to claim 14 wherein the non-polar, non-volatile emollient is selected from the group consisting of aliphatic fatty alcohols having from about 12 to about 26 carbon atoms.

17. An antiperspirant composition according to claim 16 wherein the wash-off agent is selected from the group consisting of ceteth-2 through ceteth-30, steareth-2 through steareth-30, ceteareth-2 through ceteareth-30, PEG-2 stearate through PEG-30 stearate, PEG-8 distearate, PEG-12 isostearate, C20–40 pareth-10, C20–40 pareth-40, PEG-16 hydrogenated castor oil, PEG-40 hydrogenated castor oil, and PEG-20 glyceryl stearate.

18. A process for making antiperspirant stick compositions according to claim 1, comprising the following steps:
   a. combine the solidifying agent, the liquid base material and the wash-off agent;
   b. stir the solidifying agent and liquid base material while heating until a clear homogeneous mixture is obtained;
   c. add the antiperspirant active to the clear homogeneous heated mixture;
   d. stir the mixture until uniform;
   e. pour the mixture into containers; and
   f. cool the mixture until a solid stick is formed.

19. A method of preventing formation of perspiration and malodor by applying to the underarm skin a safe and effective amount of the composition according to claim 1.

* * * * *